May 14, 1946. A. C. SODANO Plant Pat. 688
ROSE PLANT
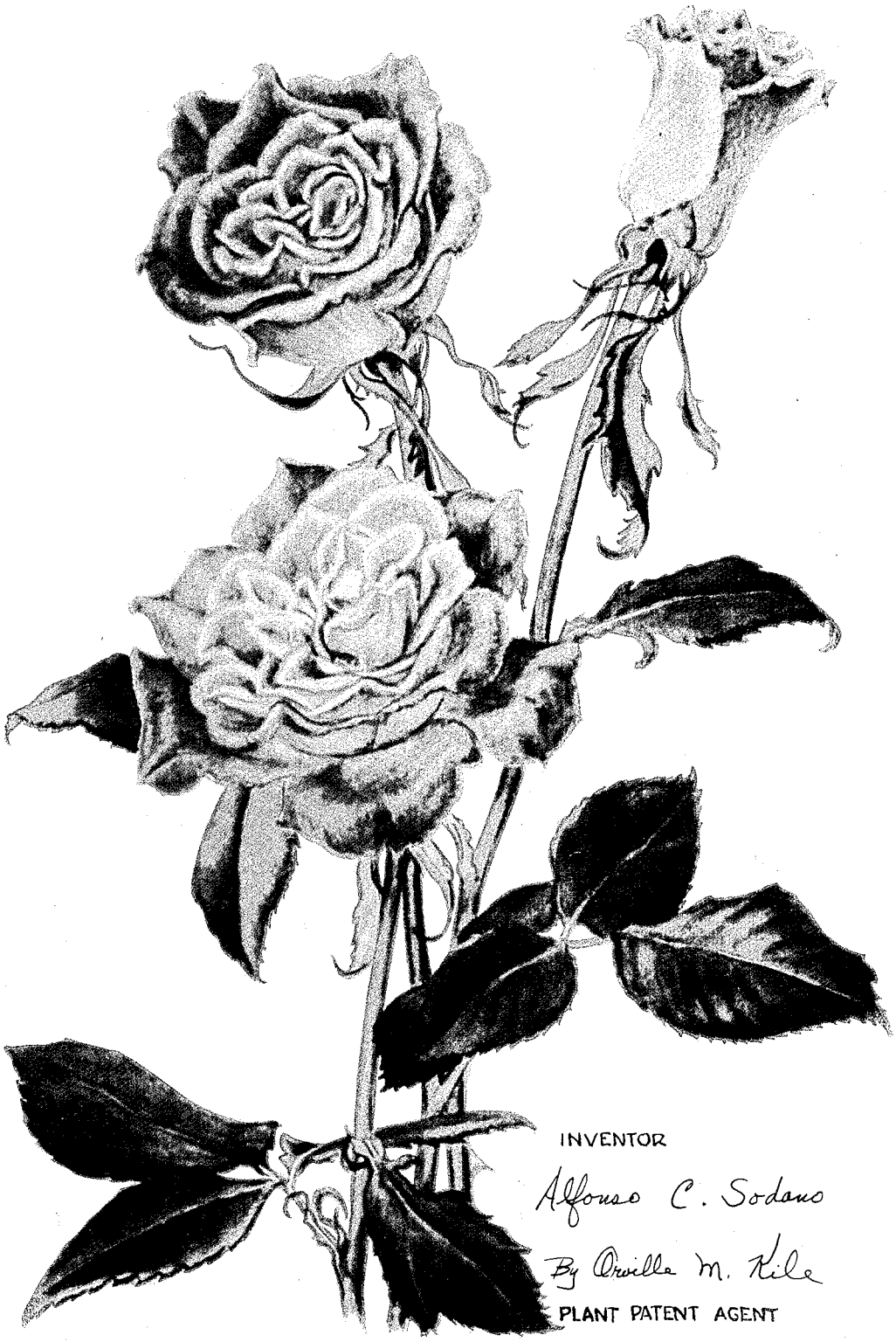
INVENTOR
Alfonso C. Sodano
By Orville M. Kile
PLANT PATENT AGENT Patented May 14, 1946

Plant Pat. 688

UNITED STATES PATENT OFFICE

688

ROSE PLANT

Alfonso C. Sodano, Bucks County, Pa.

Application July 12, 1945, Serial No. 604,683

1 Claim. (Cl. 47—61)

My present discovery relates to a new and distinct variety of rose plant with many of the features of its parent, Briarcliff, but possessing other desirable features chief of which probably is the rich dark red color of its flowers. Other outstanding distinguishing features are the heavy dark foliage, prolific production and freedom of growth, and fragrance and form of the flower.

My new variety was discovered by me as a sport of Briarcliff and has been asexually reproduced and developed by me. Its qualities have proved to be firmly fixed.

The accompanying illustration shows a half-open bud in the usual cutting stage, and two flowers in different stages of opening. Portions of the stems and foliage are also shown. All of these features are shown in as nearly the natural colors as the artist could make them although it must be understood that with the medium of water colors it is impossible to show the brilliance and sheen of the colors.

Following is a detailed description of my new variety, in which colors are designated by plate numbers of Ridgway's Color Standards and Nomenclature.

*The plant*

Growth: Very fast and free grower. Heavy and prolific producer of fine flowers.

Stems:

*Size.*—Very long and heavy. Good length obtained without pinching.

*Aspect.*—Straight and strong, holding the large flower upright.

*Internodes.*—Long.

*Thorns.*—Many; large; sharp; downward pointing; red.

Foliage:

*Leaflets.*—3 to 5 leaflets with the first below the peduncle usually a single one.

*Size.*—Large. Terminal leaflet measures up to 3½ inches long by 2 inches wide. Lateral leaflets are about 2½ inches by 1⅝ inches.

*Quantity.*—Very abundant.

*Texture.*—Heavy and leathery.

*Shape.*—Elliptical with acuminate apex. Edges finely and sharply serrated.

*Color.*—Darker than foliage of any other of the Briarcliff family. Approximately Yew Green (Plate XXXII) on the upper side, while the under side is approximately Sage Green (Plate XLVII) with frequent purplish tinge. Veins tinged red to purple, particularly on under side. New foliage is light green with red tinge.

*Stipules.*—Long; clinging but frequently have long curved points.

*Rachis.*—Stiff and substantial. Grooved on upper side and comparatively smooth on under side.

*Sepals.*—Long and foliaceous.

*The flower*

Bud:

*Size.*—Medium to large, averaging 1½ inches long just before opening.

*Form.*—Long; more pointed than bud of parent. When partly open it is urn-shaped with fluted petal edges. Shaped much like Talisman.

*Color.*—Rich dark velvety red, between Carmine and Ox Blood Red (Plate I).

*Peduncle.*—Short; straight; strong; almost completely smooth.

*Opening.*—Opens free and evenly at all seasons of the year.

Flower:

*Size.*—Large, opening to from 4½ inches to 5½ inches in diameter.

*Form.*—High centered at first, becoming deep cupshape, later opening wide and loose, and finally become peony-like. Except in the very last stages, the outer petals never droop although their edges roll loosely.

*Color.*—At first, slightly lighter than bud. As it opens it takes on some of the tones of Tyrian Rose (Plate XII) although much darker and more velvety, with something of the brilliancy of cerise. Before the flower finally withers its color takes on some of the tone of Rhodamine Purple (Plate XII). The dark velvety sheen is retained throughout the life of the flower. A notable feature is that there is absolutely no yellow aiglet but the red color is very evenly spread.

*Fragrance.*—Very decided fragrance is present.

*Petalage.*—Double, averaging about 32 petals.

*Calyx.*—Long; broad in center.

Petals:

*Size.*—Outside row of petals averages 2¼ inches long by approximately the same width at the widest point. Second row is same length but about 1½ inches wide. Next three rows about 1¼ inches wide and 1¾ inches long. Central petals much smaller.

*Substance.*—Very substantial and heavy.

*Shape.*—General shape is obovate with undulate or ruffled edge which seems to straighten out as the flower opens and the petals turn backward slightly.

*Arrangement.*—Imbricated, with petal edges slightly turned backward. Central petals are grouped over the stamens which usually remain hidden even in the later stages.

Reproductive organs:

*Pistils.*—Numerous; bunched tightly in center of pithy knob. *Styles* are Tyrian Rose (Plate XII). *Stigmas* are light tan.

*Stamens.*—Many; loosely bunched surrounding pistils. *Filaments* are Tyrian Rose (Plate XII) and of varying lengths. *Anthers* are large and light tan.

*Comparisons*

Although there are many Briarcliff characteristics in my new variety, it is distinctly different from that variety in many respects, principally as follows.

1. The color of the flower of my new variety is deep rich velvety red while that of Briarcliff is light pink.
2. My variety is a much freer and faster grower.
3. My variety is a much heavier producer.
4. My variety breaks more freely, producing longer stems.
5. Buds of my variety are more pointed and open full at all seasons of the year.
6. Foliage of my variety is heavier, larger, and darker green than that of Briarcliff or any of the Briarcliff family known to me.
7. Stems of my variety are longer and stronger.
8. There are fewer petals in my variety although they are larger.
9. My new variety is more fragrant.
10. Petals of my variety have greater substance.

The variety most like my new variety is Better Times which is also a sport of Briarcliff and the subject of Plant Patent No. 23. However the two varieties differ, principally as follows:

1. The flower of my variety is darker and more brilliant red, particularly in its earlier stages of opening.
2. The flowers of my variety are much more velvety in texture and aspect.
3. The flowers of my variety have larger petals of slightly different shape. (Petal of my variety is slightly narrower just above calyx and broader three-fourths of the way up. Outer petals of my variety are ½ inch longer.)
4. Petals of my variety have more substance.
5. My variety has fewer petals although they open in such a way as to give the impression of a large, many-petaled rose.
6. My variety is very fragrant whereas Better Times is not.
7. The calyx of my flower is a different shape from that of Better Times, being longer as well as broader in the center.
8. Petals of my flower do not droop below the calyx until the very last stages of the life of the flower, while it is the habit of Better Times to droop early.
9. The bud of my variety is more pointed.
10. The neck or peduncle of my flower is noticeably shorter, bringing the foliage closer to the flower.
11. The variety has foliage which is much heavier and has a more leathery texture.
12. My variety is a freer grower and producer when grown under similar circumstances.

Having thus disclosed my invention, I claim:

The new and useful variety of hybrid tea rose plant substantially as herein shown and described, characterized particularly by its prolific growth and production; its large dark green foliage; its long strong stems; and its large fragrant flowers of velvety dark red.

ALFONSO C. SODANO.